United States Patent
Dattilo et al.

(10) Patent No.: US 9,921,206 B2
(45) Date of Patent: Mar. 20, 2018

(54) INTEGRATED AND INTELLIGENT PAINT MANAGEMENT

(71) Applicant: PPG Industries Ohio, Inc., Cleveland, OH (US)

(72) Inventors: Vincent P. Dattilo, Medina Township, OH (US); Charles J. Beyer, New Kensington, PA (US); Christian J. Decker, Wadsworth, OH (US); Thomas M. Riley, Fair Haven, MI (US)

(73) Assignee: PPG Industries Ohio, Inc., Cleveland, OH (US)

( * ) Notice: Subject to any disclaimer, the term of this patent is extended or adjusted under 35 U.S.C. 154(b) by 324 days.

(21) Appl. No.: 14/695,459

(22) Filed: Apr. 24, 2015

(65) Prior Publication Data

US 2016/0313294 A1    Oct. 27, 2016

(51) Int. Cl.

| | |
|---|---|
| *G01N 37/00* | (2006.01) |
| *G01N 33/32* | (2006.01) |
| *B05B 12/00* | (2018.01) |
| *G06Q 10/06* | (2012.01) |
| *G06Q 10/10* | (2012.01) |

(52) U.S. Cl.
CPC ............ *G01N 33/32* (2013.01); *B05B 12/00* (2013.01); *G06Q 10/06* (2013.01); *G06Q 10/10* (2013.01)

(58) Field of Classification Search
None
See application file for complete search history.

(56) References Cited

U.S. PATENT DOCUMENTS

| | | | |
|---|---|---|---|
| 6,528,109 B1* | 3/2003 | Filev | B05B 12/084 118/313 |
| 2005/0096796 A1* | 5/2005 | Filev | G05B 13/027 700/283 |
| 2010/0033318 A1 | 2/2010 | Tampke | |
| 2012/0123583 A1 | 5/2012 | Hazen et al. | |
| 2012/0219699 A1 | 8/2012 | Pettersson et al. | |

FOREIGN PATENT DOCUMENTS

EP    0915401 A2    5/1999

\* cited by examiner

*Primary Examiner* — Aditya Bhat
(74) *Attorney, Agent, or Firm* — Michael J. Frodsham

(57) ABSTRACT

Methods, systems, and computer readable-medium with instructions for receiving data and providing calculated adjustments to a paint application process can comprise receiving at the server a first operating parameter associated with a first paint processing machine at a first painting facility. The method can also comprise receiving at the server a first quality control measurement from an analysis of a finished first paint product. Additionally, the method can comprise accessing from a database a set of historical operating parameters associated with the first painting processing machine. Further, the method can comprise automatically identifying a deficiency in the finished first paint product based upon the first quality control measurement. Further still, the method can comprise transmitting to a mobile computing device screen a proposed adjustment to the first operating parameter that will correct the deficiency.

28 Claims, 12 Drawing Sheets

FIG. 4

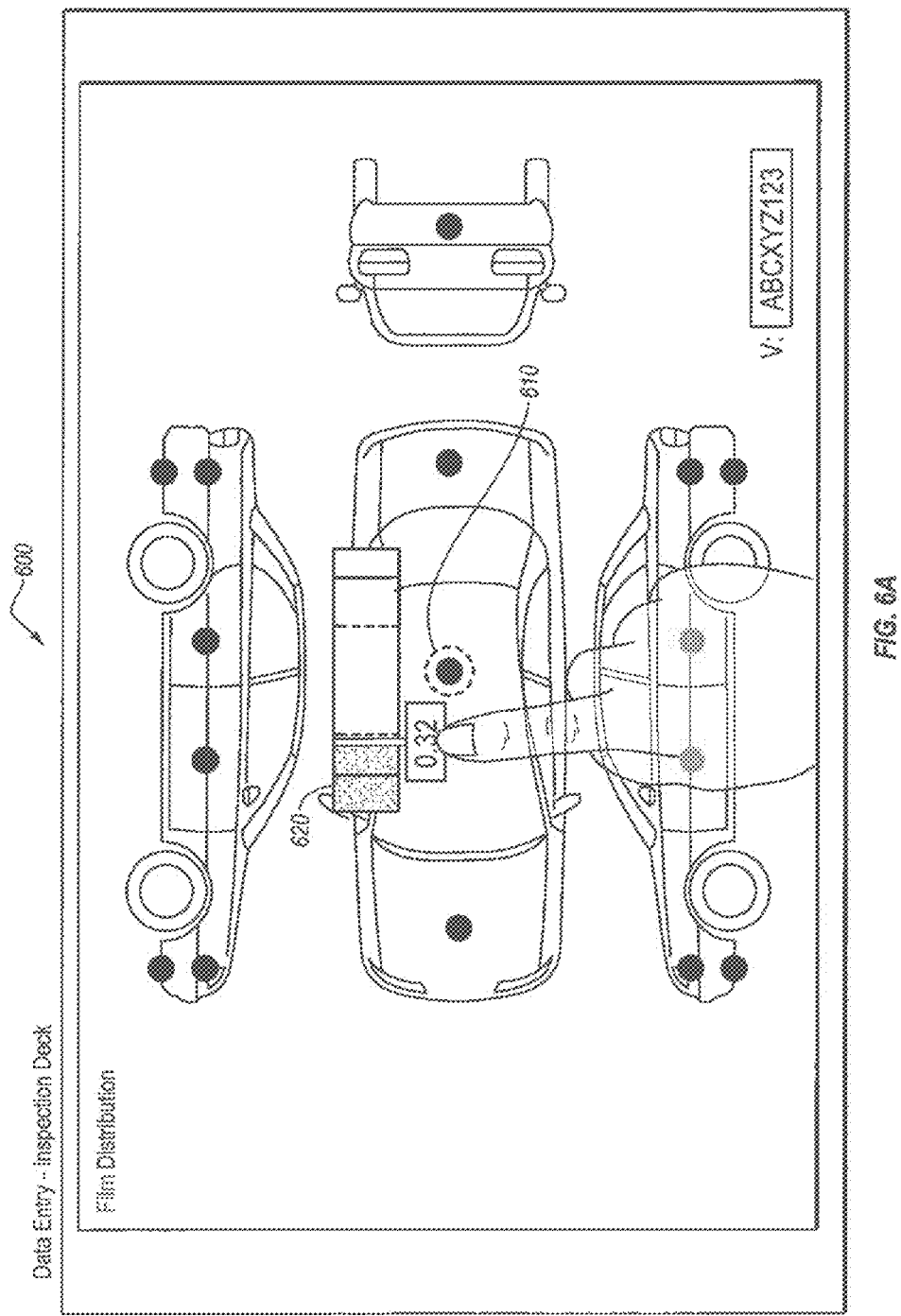

FIG. 7C

INTEGRATED AND INTELLIGENT PAINT MANAGEMENT

BACKGROUND OF THE INVENTION

Many modern industrial painting processes involve highly complex multi-step processes. For example, automotive, commercial vehicle, aerospace, light & heavy industrial, marine, and others require highly consistent coatings film thickness, final paint colors, visual appearance equal to expectation, cured coatings performance properties equal to specification, across large product lines and over long periods of time. This is further complicated by modern painting methods that often involve multiple layers and complex chemistry.

For example, in some conventional systems, each of the coating layers can be additive and build upon one another. Additionally, many of the layers may be polychromatic color and clear finishes. As such, it is increasingly difficult and important to ensure that each layer is consistent across the process so that the final product has the correct coating attributes. For example, a single car may be painted with multiple different layers in order to provide significant corrosion protection and create a very specific final color and effect. A significant discrepancy within any of the layers may result in a final paint color that does not meet the specifications and that does not match the other cars, or final cure film performance does not meet quality or durability specifications.

Additionally, conventional systems often require unique paint formulations for different geographic locations or regional legislative requirements in order to create coatings that have the same specifications and/or attributes. Further, in some cases, significant changes in local environmental conditions can impact the paint application process. The unique formulations and the impacts of weather present multiple problems relating to color and appearance consistency and costs. For example, as conditions change at one facility the color may drift away from the color produced by the other facilities.

Further, due to the complexity of the paint application process, it can be extremely difficult to identify what parameters need to be adjusted in order to create a final paint coating that is within the specifications. Within conventional paint systems, when a problem is identified, a specialist at the facility relies upon their own personal experience and the "art" of the paint application process to identify the potential problem. This solution is undesirable because different specialists will have different experience and different exposure to the various paint application process. As such, different specialists may respond differently to the same problem and unintentionally create further problems within the paint application process.

Accordingly, there are many problems in the art to be addressed.

BRIEF SUMMARY OF THE INVENTION

The present invention can comprise a first system for monitoring a paint application process at a first facility. The first system can alert human intervention for or automatically adjust paint parameters within a first multivariate paint application system based upon sensor or device data gathered from various first sensor or device modules. The first system can also comprise a quality assurance parameter database. The quality assurance parameter database can be configured to provide an indication of an ideal range of a final paint product attribute. The first system can further comprise an electronic sensor module operated via human interface or configured to automatically measure the final paint product attribute on a completed product.

Additionally, the first system can also comprise a quality assurance processing module. The quality assurance processing module can be configured to receive the measured final paint product attribute from the electronic sensor module over a network. The quality assurance processing module can be configured to determine that the measured final paint product attribute is outside of the ideal range. Additionally, the quality assurance processing module can be configured to access a database of one or more operating parameters and one or more paint mixture ingredients. Further, the quality assurance processing module can be configured to determine, using a first multivariate analysis, at least one of the one or more first operating parameters that if adjusted would place the final paint product parameter for future products within the ideal range. The multivariate analysis can account for at least current environmental conditions, machine operation parameters, and paint ingredients and condition.

Additionally, the present invention can comprise a method for receiving data and providing calculated adjustments to a paint application process. The method can further comprise receiving at the server a first operating parameter associated with a first paint processing machine at a first painting facility. The method can also comprise receiving at the server a first quality control measurement from an analysis of a finished first paint product. Additionally, the method can comprise accessing from a database a set of historical operating parameters associated with the first painting processing machine. Further, the method can comprise automatically identifying a deficiency in the finished first paint product based upon the first quality control measurement. Further still, the method can comprise transmitting to a mobile computing device screen a proposed adjustment to the first operating parameter that will correct the deficiency.

Additional features and advantages of the present invention will be set forth in the description which follows, and in part will be obvious from the description, or may be learned by the practice of the present invention. The features and advantages of the present invention may be realized and obtained by means of the instruments and combinations particularly pointed out in the appended claims. These and other features will become more fully apparent from the following description and appended claims, or may be learned by the practice of the present invention as set forth hereinafter.

BRIEF DESCRIPTION OF THE DRAWINGS

In order to describe the manner in which the above recited and other advantages and features of the invention can be obtained, a more particular description of the invention briefly described above will be rendered by reference to the present invention, which is illustrated in the appended drawings. Understanding that these drawings are not to be considered to be limiting of the scope of the present invention, the invention will be described and explained with additional specificity and detail through the use of the accompanying drawings in which:

FIG. 4 depicts another paint system user interface in accordance with the present invention;

FIG. 6A depicts another paint system user interface in accordance with the present invention;

FIG. 7C depicts another paint system user interface in accordance with the present invention;

DETAILED DESCRIPTION

Figure 1:
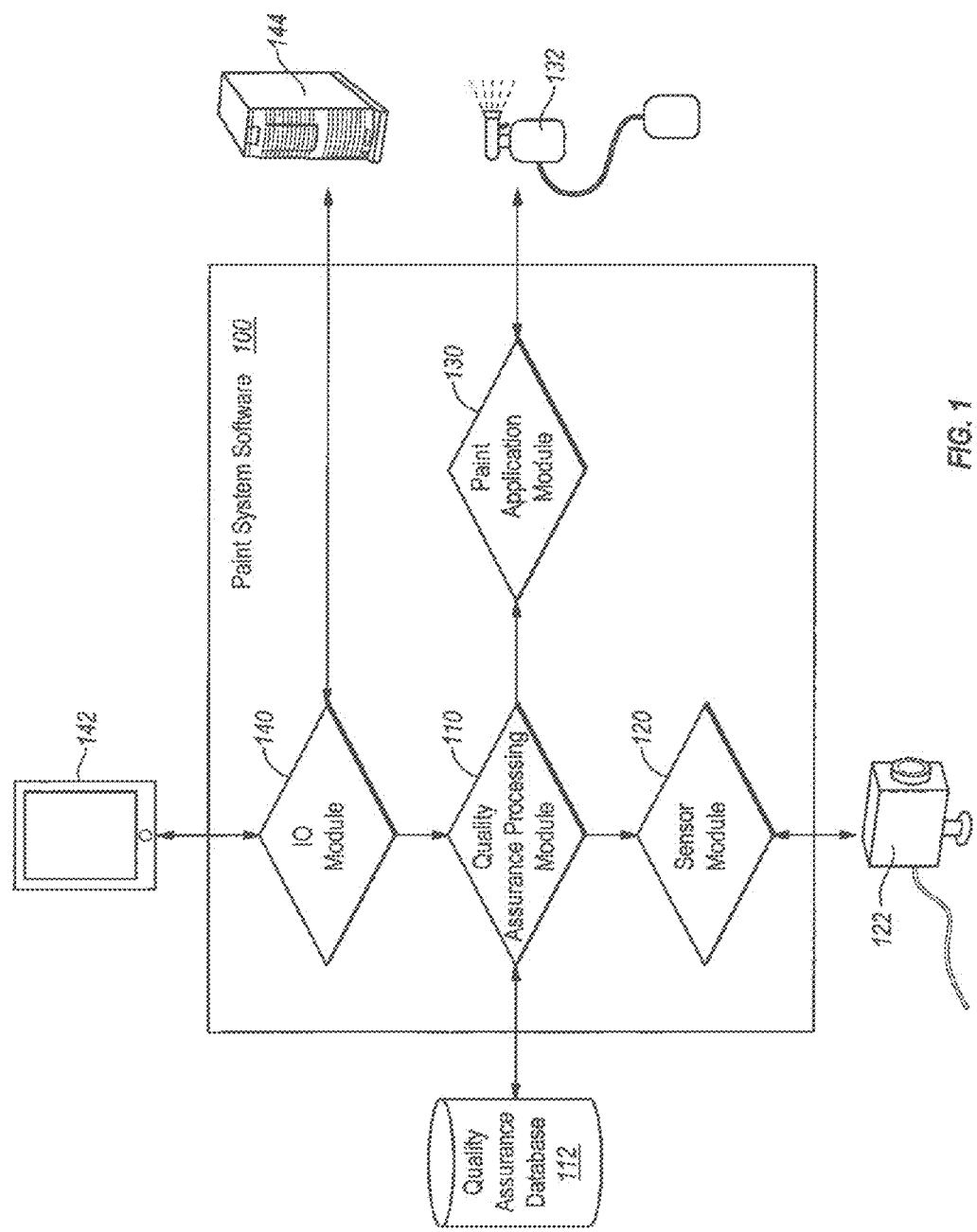
FIG. 1 illustrates a schematic diagram of a computer system in accordance with the present invention.

The present invention extends to systems, methods, and apparatus configured to automatically or with human interface gather diverse data from a paint facility and identify one or more paint or applications process parameter attributes that could place a final cured film painted product outside a desired range. In particular, the present invention can comprise various computing modules and/or sensor modules configured to receive sensor readings or human input device readings and then analyze all variables to validate current or create proposed adjusted operating parameter changes. The sensor or device readings can comprise both current operating parameters and environmental data. Additionally, data can be shared across multiple, geographically-diverse painting facilities such that paint formulations and output can be optimized.

Accordingly, the present invention can provide significant technical advances and address long felt needs within the field of large-scale paint application. For example, the present invention can provide an intuitive interface for managing a complex paint application process. Additionally, the present invention can provide automatic computer-based learning suggestions for preemptively correcting potential problems within the paint application process. Further, the present invention can provide methods for optimizing paint processes across a variety of geographically diverse paint facilities.

When applying paint and other coatings to a particular product, granular tracking and control of each independent step can be vital. For example, the final coating performance can be heavily dependent upon the process control and consistency with which each individual layer and coating is applied, dried, or otherwise cured. One will understand that if any step in the paint application process varies significantly outside of a threshold value, the finished paint coating may fall outside of desired specifications.

Identifying and maintaining the proper coating chemistry can be a critical step in deriving or achieving the desired final film performance properties. Coatings chemistry and painting processes, however, have grown ever more complex. The increased complexity has, at least in part, been due to more strenuous customer specifications, societal demand for lower total environmental impacts, cost driven toward lower consumption of energy, and high quality demands.

As coating specifications and complexity have increased, the conventional artisan-based approaches for managing paint facilities have become inadequate and inefficient. In particular, those of common knowledge in the painting industry recognize there are relationships between the coatings chemistry, the applications and processes applied, and the final painted product. Despite this recognition, conventional methods fail to demonstrate or utilize a dynamic understanding of paint controlling and monitoring of the diversity of variables within a paint facility. For instance, conventional methods may include a paint manager identifying a particular problem in the paint process and relying upon his own personal experience, guessing what process should be changed to correct the problem.

The present invention can incorporate multiple variables with respect to paint chemistry, including but not limited to chemistry type, solids, solvency, viscosity, rheologies, shear behavior, pressure, flow, temperature, and the like. Similarly, the present invention can incorporate multiple variables with respect to paint applications and cure processes. These variables can include, but are not limited to, painting process type, coating through-put rate, speed of coating deposit, climatic conditions, pressures, flows, voltages, temperatures, atomizers and atomization energies, evaporation energies, cure energies, and the like.

In particular, each of the aforementioned variables can be monitored to determine if they fall within one or more defined thresholds. The invention can comprise a mobile computing device, which can be configured to do the variable monitoring and analysis of input data to define the system health and paint process quality outcomes. The data collection can take a variety of different forms, including but not limited to human input, automatic communication from process control equipment, near field communication or data capture, input from measurement instruments, cameras, bar or QR readers, voice recording, or other input methods. Once entered, algorithms that can predict paint process outcome based on the range of multivariate inputs can analyze the data.

Along these lines, FIG. 1 depicts a paint system that includes paint system software 100. As depicted, the paint system software 100 can comprise various modules and components. One will understand, however, that the modules and components shown and described herein are provided only for the sake of clarity and explanation and do not limit the system to any particular configuration. In particular, other paint system software 100 may otherwise divide, combine, or describe the various modules and still remain within the scope of the present invention. Additionally, in various implementations, modules can comprise hardware components, software components, or combinations of hardware and software components.

FIG. 1 shows that the paint system software 100 can be in communication with a quality assurance database 112, various sensor units 122, various paint production machinery 132 (e.g., spray applicators, paint baths, ovens, etc.), various mobile computing devices 142, and various remote servers 144. When in use, the paint system software 100 can both receive information regarding a painting process and propose various changes and optimizations based upon the received information.

FIG. 1 further shows that the paint system software 100 may also comprise a quality assurance processing module 110. The quality assurance processing module 110 may further be in communication with various other modules 120, 130, 140 and components 112 within a paint system. For example, the quality assurance processing module 110 can receive sensor data from various sensor modules 120. For instance, a sensor module maybe in communication with a camera or spectrophotometer 122. The camera or spectrophotometer may be configured to identify a final paint product attribute such as film thickness, color, or finish appearance attributes on a finished paint product. Additionally, the sensor module 120 may also be in communication with various other sensors including but not limited to thermometers, pressure sensors, depth sensors, chemical detection sensors, multi-meters, and other paint process related sensing devices.

Additionally, the quality assurance processing module 110 can receive input information from a user through a mobile computing device 142. For instance, a user can manually enter various data points and sensor readings into the mobile computing device 142 as the data points and sensor readings become available to the user. Instead of using a mobile computing device such as a tablet or a smartphone, a user can utilize a desktop computer, a server, or any other user operated computing device to interact with the paint system software 100.

Once the quality assurance processing module 110 has received one or more data points, the quality assurance processing module 110 can receive specific production information from a quality assurance database 112. For example, the quality assurance database 112 can comprise various paint specifications that describe desired or ideal final paint attributes. Additionally, the quality assurance database 112 may also comprise various operating threshold information that describes acceptable thresholds for various processes within the painting system. For example, it may be desirable to apply a certain thickness of a coating, a certain viscosity of a coating, or to apply a coating at a particular temperature.

The quality assurance processing module 110 can identify various problems within the paint application system. For example, the quality assurance processing module 110 can identify an undesirable trend detected by the sensor module 120. Similarly, the quality assurance processing module 110 can detect when a predetermined threshold has been breached.

Based upon the detected undesirable behavior or predicted undesirable outcome, the quality assurance processing module 110 can propose specific changes needed to correct the problem. For example, the quality assurance module 110 can send a proposal to input/output ("IO") module 140, which can then forward the proposal to the appropriate user. In relation to the present invention, multiple users may have access to different computing devices 142. The I/O module 140 may selectively send the proposed solution to a particular user that is associated with a particular point in the paint process. For example, a proposal may relate to a pre-paint process. The I/O module 140 may identify a user in charge of the pre-paint process and send the proposal only to that user.

Alternatively, the quality assurance processing module 110 can automatically execute the proposed change by communicating directly with a paint application module 130. For example, the paint application module 130 may be in communication with a variety of different paint application machinery 132. For example, the paint application module 130 may be in communication with a paint applicator 132, such as an automated atomizer, a paint air gun, an electrostatic spray gun, a bell sprayer, or some other paint applicator. Accordingly, upon receiving the proposed change, the paint application module 130 can automatically control the paint applicator 132 to implement the proposed change. For example, the proposed change may comprise an increased spray rate. In this case, the paint application module 130 can increase the spray rate of the paint applicator 132. One will understand, however, that any machinery or system within the paint facility may also be operable by the paint application module 130.

Additionally, quality assurance processing module 110 can rely upon a multivariate analysis when determining proposed changes. For example, the quality assurance processing module 110 may rely upon current local meteorological conditions, multiple sensor readings, specific information relating to the type and make of various paint application machinery 132, and information relating to various components of a paint formulation. The quality assurance database 112 can provide the information relating to paint formulation, paint application machinery type, paint application machinery make and model, and other similar information.

Additionally, The quality assurance processing module 110 can adjust and revise one or more equations used within the multivariate analysis. For example, the multivariate analysis may comprise components that are weighted based upon historic feedback received by the paint system software 100. For example, based upon analyzed historic feedback data, the quality assurance processing module 110 may identify that a particular chemical component varies based upon heat and pressure. Using the identified relationship, the quality assurance processing module 110 can propose solutions and actions necessary to correct or modify various final paint product attributes.

Over time, however, as machinery within the paint facility is replaced or repaired, one or more paint application variables may intentionally or unintentionally vary from their historic value. The quality assurance processing module 110 can identify that one or more sensors are providing feedback that does not align with historical parameters. Based upon the unexpected feedback, the quality assurance processing module 110 can automatically learn and adjust the multivariate analysis to account for the adjusted parameters. Additionally, the present invention can determine when a particular sensor is inoperative or returning erroneous readings. For example, upon receiving a reading that significantly exceeds an expected threshold, the present invention can flag the associated sensor as needing inspection.

Additionally, the quality assurance module 110 can identify previously unknown associations and trends between paint production variables. For example, using machine-learning techniques, the quality assurance module 110 may identify previously unknown relationships between local humidity, particular chemicals within a paint formulation, and paint curing characteristics.

After identifying these relationships, the quality assurance module 110 can incorporate these relationships into future proposed changes. For instance, the quality assurance module 110 may identify that due to a change in humidity and its impact on a particular chemical within a paint formulation, that an atomizer should be adjusted to ensure the paint meets the required specifications. Accordingly, the present invention can automatically identify relationships that are unknown in the conventional art and can automatically propose changes to a paint application process based upon the identified relationships.

Additionally, the paint system software 100 may also communicate through the I/O module 140 with a remote server 144. Remote server 144 may, for example, comprise a central processing hub (e.g., FIG. 2) that is in communication with multiple instances of paint system software 100 spread across multiple geographically diverse paint facilities.

Figure 2:
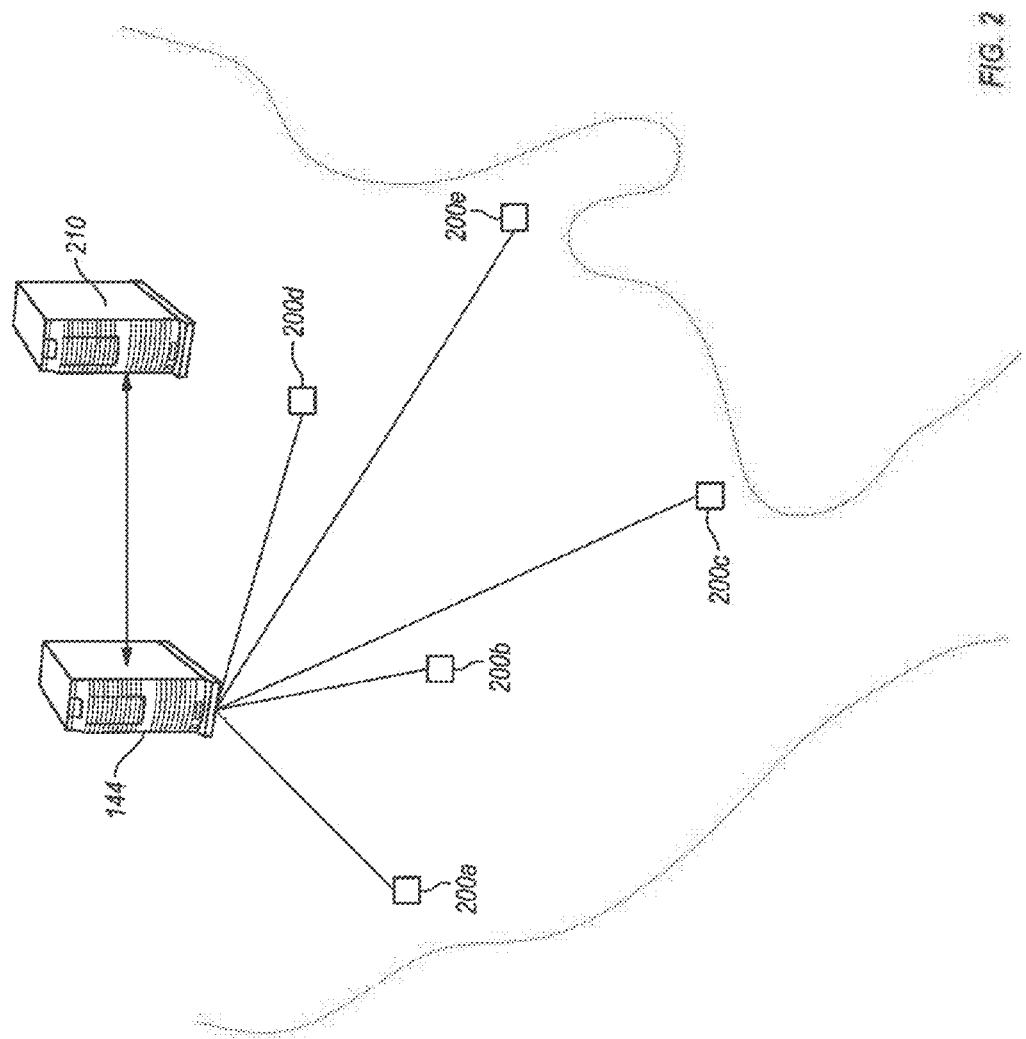
FIG. 2 illustrates a schematic diagram of a remote server communicating with geographically diverse paint facilities in accordance with the present invention.

For example, FIG. 2 depicts a schematic diagram of a remote server 144 in communication with multiple paint facilities 200(a-e). The remote server 144 can receive various sensor readings, coating output quality data, and process data from the various paint facilities 200(a-e). Using this information, the remote server 144 can identify trends at each of the respective paint facilities 200(a-e). Additionally, remote server 144 can identify optimizations that can be pushed out to the various facilities. For example, remote server 144 can identify how to adjust the paint manufacturing and application process to accommodate for humidity changes at a particular paint facility 200e that is in a humid region. The remote server 144 can then automatically provide the adjustments to a different paint facility 200b within a second region that is experiencing uncommonly high humidity for the second region.

As such, the present invention can provide significant benefits over the conventional "artisan" approach to paint application. Specifically, the present invention can accommodate variation or limitations knowledge of the individual in charge of a shift. For example, the shift leader in one region versus another region may have little or no experience dealing with excessive humidity. Since, the present invention can share information across diverse geographic regions and climates, systems of the present invention can provide optimizations and adjustments that previously were not possible.

Additionally, the present invention provides systems and methods for consolidating paint formulations across multiple geographically diverse locations. For instance, a particular color of blue created at paint facility 200a may require a unique and different paint formulation than facility 200e to create the same color of blue. One will understand the significant technical and financial difficulties implicated in creating unique paint formulations for every paint facility so that uniform colors can be achieved across the facilities 200(a-e).

Further, the present invention provide high adaptation to changing weather patterns at the individual facilities, changing and upgrading machinery at the individual facilities in both the form of a piece-meal upgrade and a entire facility upgrade, and accurately tracking specific outcomes at the different facilities. In contrast to the shortcomings of the conventional art, present invention can automatically identify common trends and differences among the various different paint facilities 200(a-e) without regards to differences in machinery, weather, and other local variables. Using this information, significant improvements in paint coating quality and efficiency can be automatically implemented.

For example, the remote server 144 can identify paint formulations that can be commonly used by multiple paint facilities 200(a-e) to create coatings that meet the same final specifications or attributes. For instance, a particular paint formulation may be used in paint facility 200a to create a particular color of green. Using information received from both paint facility 200a and paint facility 200e, the remote server 144 can identify that paint facility 200e uses the same paint formulation as paint facility 200a but with different facility operating parameters to create the same color of green. As such, remote server 144 can save costs by sending the same paint formulation to both facilities 200a, 200e and allowing the local quality assurance processing modules 110 to make the necessary unique adjustments at each facility 200a, 200e to create the correct coating.

In addition, the remote server 144 can also automatically manage inventory at an inventory server 210 based upon the information received from the various paint facilities 200 (a-e). For example, remote server 144 may identify that a particular chemical component at a particular paint facility is running low. The remote server 144 may be able to automatically initiate an order for that chemical before it runs out at the paint facility.

Additionally, the remote server 144 can automatically adjust paint production based upon detected changing weather patterns and/or other parameters. For example, the remote server 144 may receive weather forecast information for one or more of the locations of the paint facilities 200(a-e). Further, the remote server 144 may identify that a weather trend that is occurring or is forecasted to occur at a particular paint facility 200a, and will have a detrimental effect on a particular coating that the paint facility 200a is supposed to produce. Upon making this determination, the remote server 144 can automatically shift the paint orders from the paint facility 200a that is affected with the detrimental weather to another paint facility 200b that is not experiencing or otherwise affected by the detrimental effects.

The use of the remote server 144 within this description is meant to only indicate that a computing module is remote from at least one of the painting facilities. One of the paint facilities may host the remote server 144 such that the other paint facilities are all communicating with the single hosting facility. Alternatively, the remote server 144 may be simultaneously hosted by multiple paint facilities 200(a-e), or even all the paint facilities 200(a-e), through a distributed system.

As discussed above, the present invention can also include mobile computing devices 142. The mobile computing devices 142 can be both input devices and output devices. For example, a paint technician may input various paint variables into the mobile computing device 142. The input variables may then be provided to the paint system software 100.

Additionally, a mobile computing device 142 can be used to display proposed changes generated by the quality assurance processing module 110. For example, a technician working in the pre-paint portion of a paint facility may receive a proposed change to adjust a particular aspect of the pre-paint process. Accordingly, a mobile computing device 142 can provide unique and novel ways for technicians in charge of specific areas in a paint facility to receive proposed changes that account for conditions and variables throughout the entire paint facility process. Similarly, the present invention can provide paint facility managers with quick and easy access to information relating to the entire paint facility.

Figure 3:
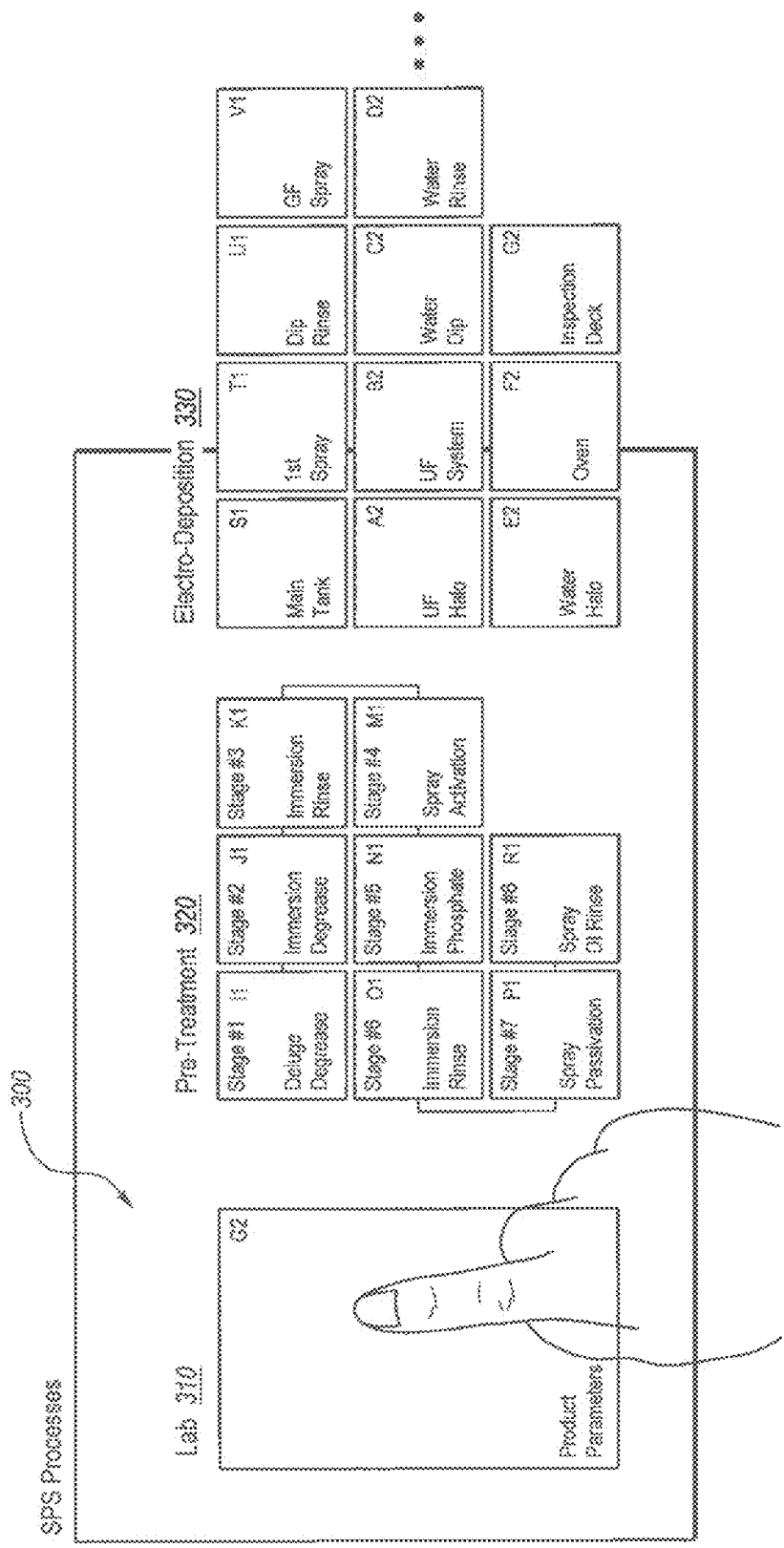
FIG. 3 depicts a paint system user interface in accordance with the present invention.

For example, FIG. 3 depicts a user interface 300 composed of icons 310, 320, 330 representative of different aspects of a paint application process. The icons can include a lab icon 310, a pre-treatment set of icons 320, an electro deposition set of icons 330, and any number of other icons necessary to represent different portions of the paint process. As such, using the user interface 300 of FIG. 3, a user can quickly and easily access information relating to any individual portion of a paint process.

Figure 4:
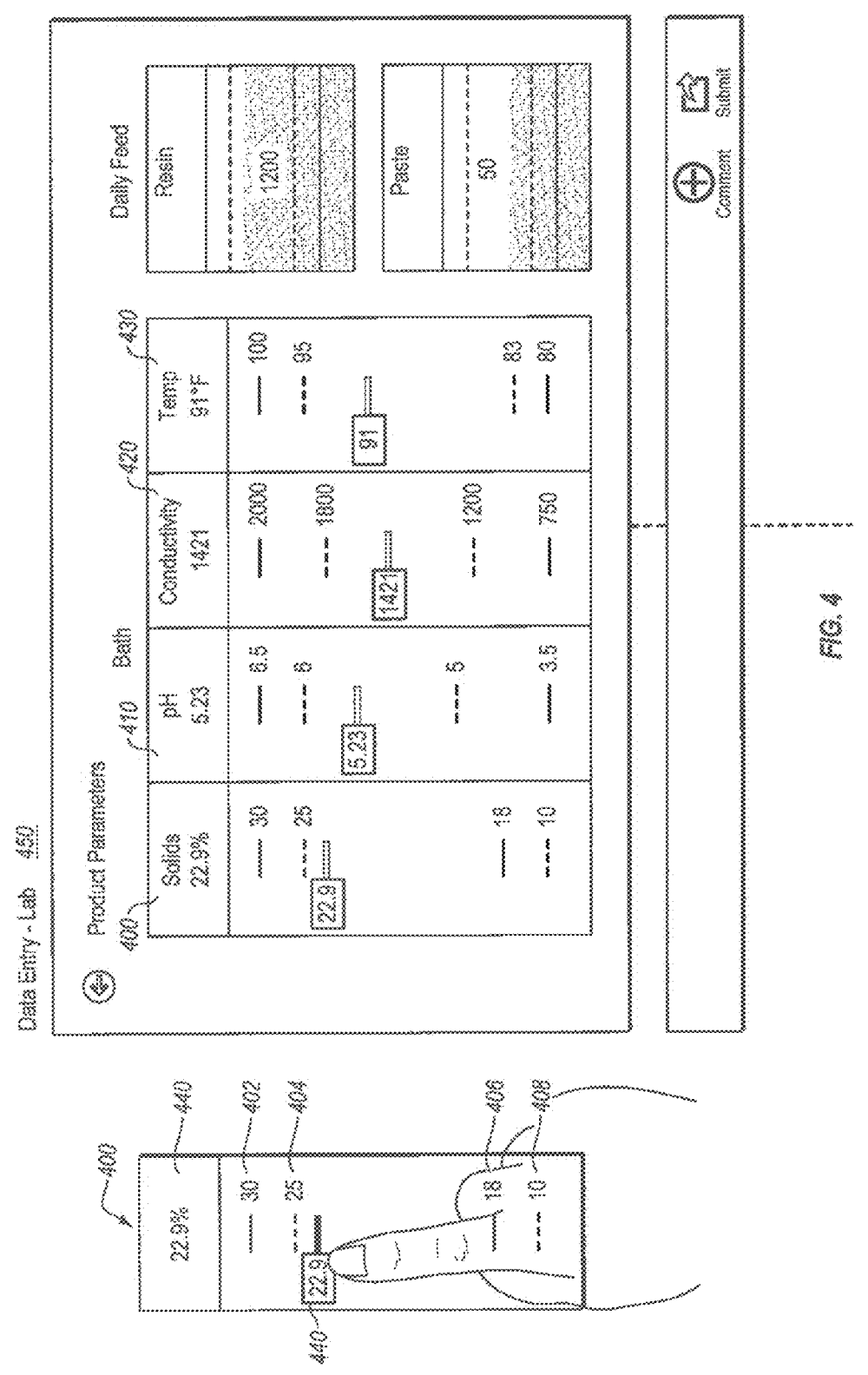

For instance, upon selecting the lab icon 310, a lab interface 450 may be displayed to a user as depicted in FIG. 4. The lab interface 450 may comprise various inputs and outputs relating to a paint formulation chemistry. For example, the exemplary lab interface 450 of FIG. 4 comprises a solids chart 400, a PH chart 410, a conductivity chart for 20, a temperature chart 430, and other various information charts.

FIG. 4 also displays an exploded view of the solids chart 400 depicting a current state number indicator 440 along with various thresholds 402, 404, 406, 408. The current state indicator 440 may indicate the current detected percentage of solids. Additionally, the current state indicator may also indicate a user-specified percentage of coating solids. For example, a user may select the current state indicator 440 and adjust the number to reflect a desired level of paint solids within the coating.

FIG. 4 shows that as a user adjusts the requested solids amount 440, indicators relating to the other display variables 410, 420, 430 may automatically adjust themselves to reflect detected changes in each of the respective levels or to display calculated changes within each of the respective levels. Accordingly, the information displayed within the user interface 450 can be dynamically updated to reflect sensed data, dynamically updated to represent calculated data, and/or manually adjusted by a user.

As an example of a user adjusting a value within the user interface 450, the quality assurance processing module 110 may suggest that a user decrease the percentage of solids from 22.9% to 21.3%. The reason for the suggested change may not directly relate to an incorrect percentage of solids, but may instead relate to a causal relationship that is not apparent until further into the painting process. As such, the adjustment of the solid percentage may not have a discernible effect to the user actually making the adjustment, but may correct a potential problem further in the process.

The user interface can also comprise thresholds 402, 404, 406, 408. The thresholds may indicate limits for safety factors, quality factors, and other such limits. For example, a first upper threshold 404 may indicate a threshold that can only be crossed for a specific period of time. A second upper threshold limit 402 may indicate a level that should never be crossed due to safety concerns. Accordingly, a user viewing the sensed current indicator 440 can immediately determine whether the indicator is within a desired threshold. Similarly, a user adjusting a current indicator 440 can clearly and easily know acceptable ranges of adjustment.

Figure 5:
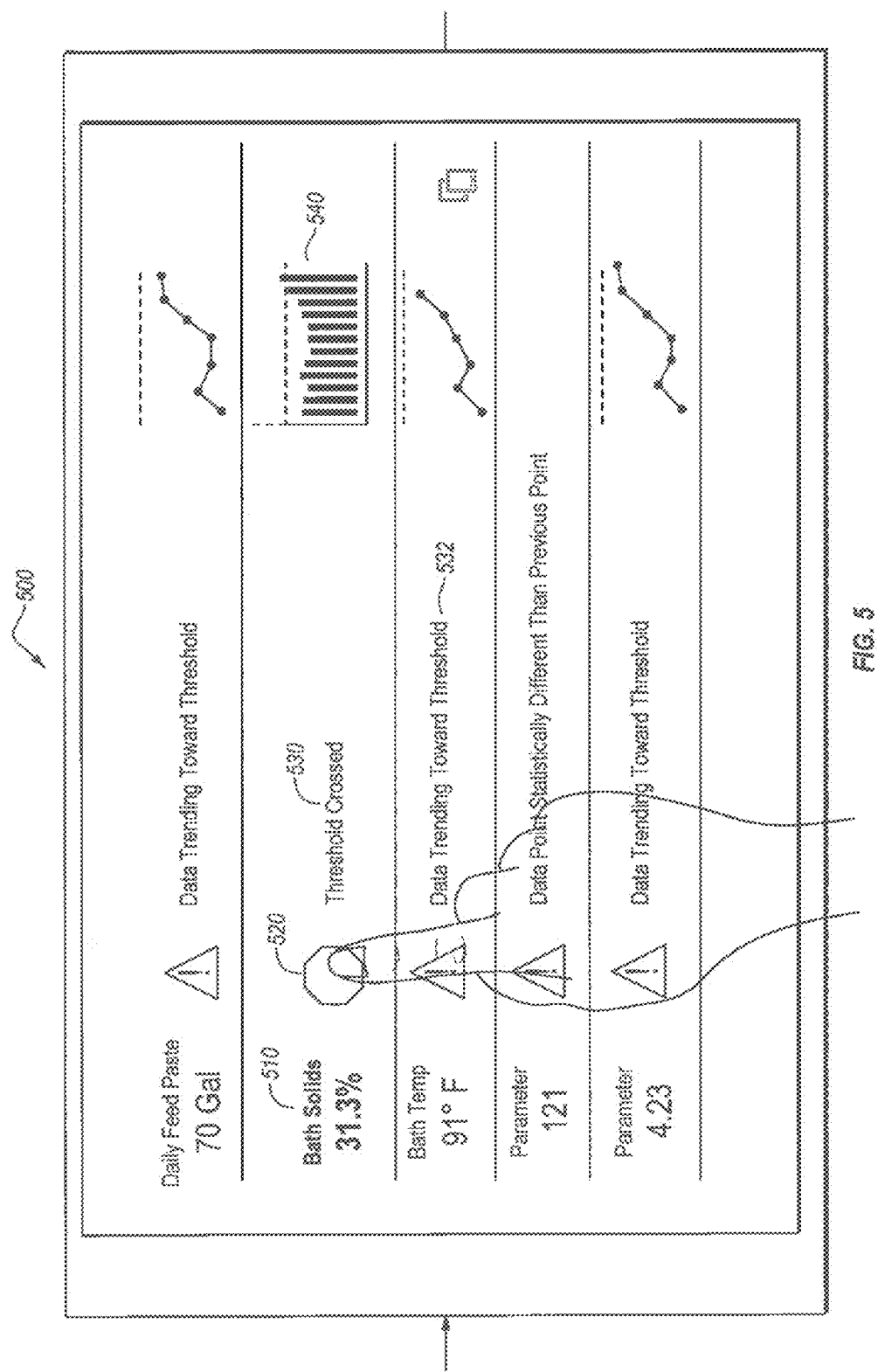
FIG. 5 depicts another paint system user interface in accordance with the present invention.

FIG. 5 depicts an action item user interface 500. As shown, the action item user interface 500 can comprise various warnings relating to current paint facility operation. The warnings can be filtered by the individual user who is accessing the action item interface 500. For instance, a user associated with the curing process will only be displayed warnings that are within the user's ability to control.

The action item interface 500 may also comprise an icon warning indicator 520 that visually displays to a user the importance of a particular indication. For instance, the action item interface 500 comprises exclamation marks for warnings and stop signs for critical items. Additionally, the action item interface may comprise a numerical indication 510 displaying the sensor reading that is a cause of concern. Further, the interface 500 may comprise a brief description 530 of the present problem. The brief description may further comprise graph or other numerical depiction of the previous sensor readings 540.

One will appreciate that the action item interface 500 may comprise warnings for readings of crossed thresholds 530, for readings that are trending towards thresholds 532, for statistical anomalies between concurrent readings, and for other problems analytically identified by the quality assurance processing module 110. A user can access further information relating to each warning by simply selecting the warning within the action item interface 500. Once a warning is selected, a user may be presented an interface similar to the interface of FIG. 4 described above.

In addition to receiving warnings through the action item interface 500 a user can also input warnings and problems into the system. For example, FIG. 6 depicts a problem reporting user interface 600 for reporting particular problems identified within a finished product. The finished product depicted in FIG. 6 comprises an automobile. For example, upon identifying that a coating thickness for the roof of a car is insufficient, a user can select the roof of the car 610 and indicate on a graph 620 the detected problem. This and similar interfaces may be necessary to enter data that the sensors are unable to automatically gather. Additionally, this and similar interfaces may be necessary to further explain sensor data.

Figure 6B:
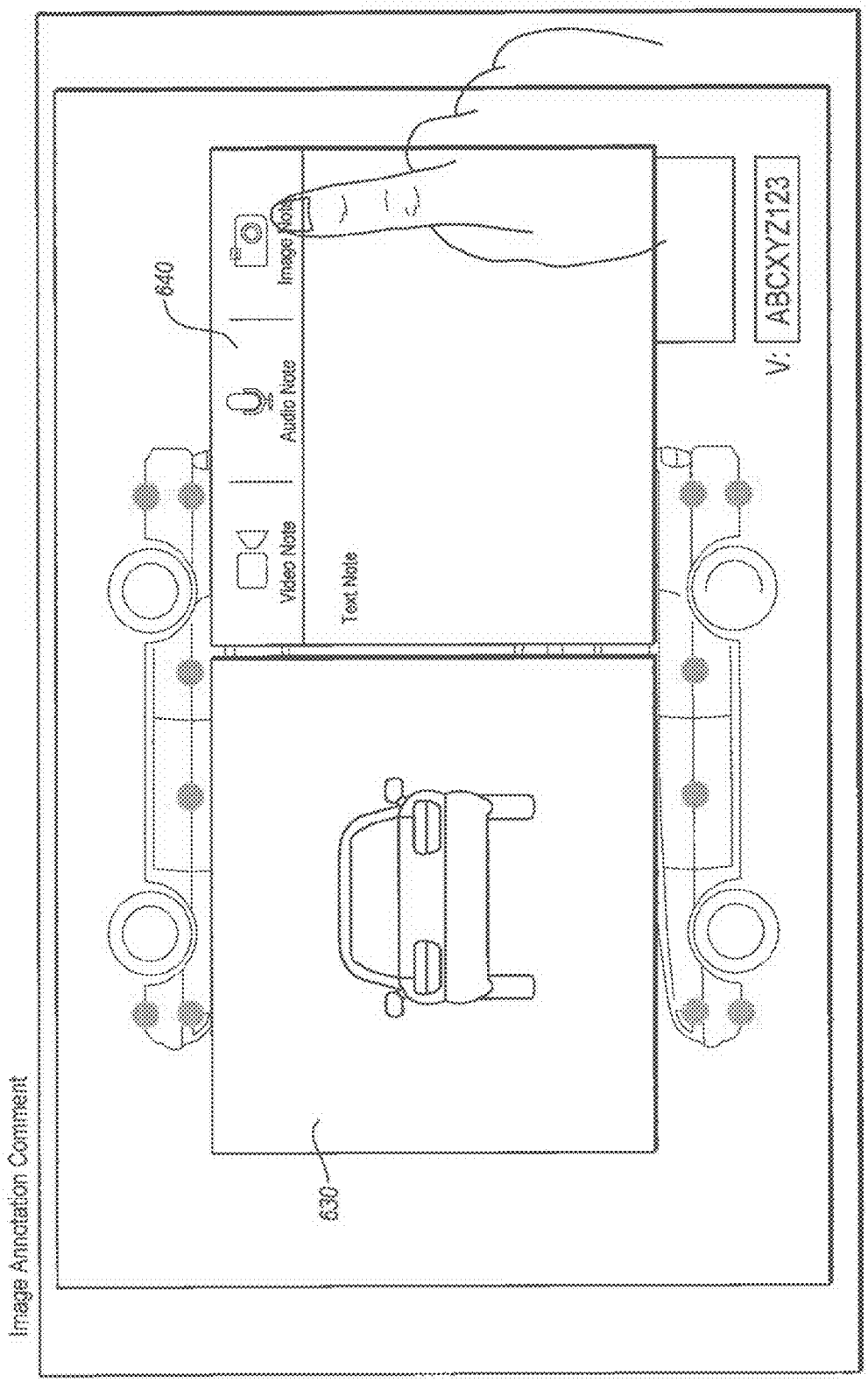
FIG. 6B depicts another paint system user interface in accordance with the present invention.

For example, FIG. 6B depicts a user data entry interface 630. The user data entry interface 630 can comprise a sketch portion where a user can draw on a picture of a finished product and enter text regarding the finished product, a picture portion where user can take a picture of the problems with the finished product, a video portion, an audio recording portion, and other portions for any other data input means. Using the user input interface 630, a user can articulate a problem and submit the problem such that a paint facility manager or troubleshooter can review the user's notes.

Figure 7A:
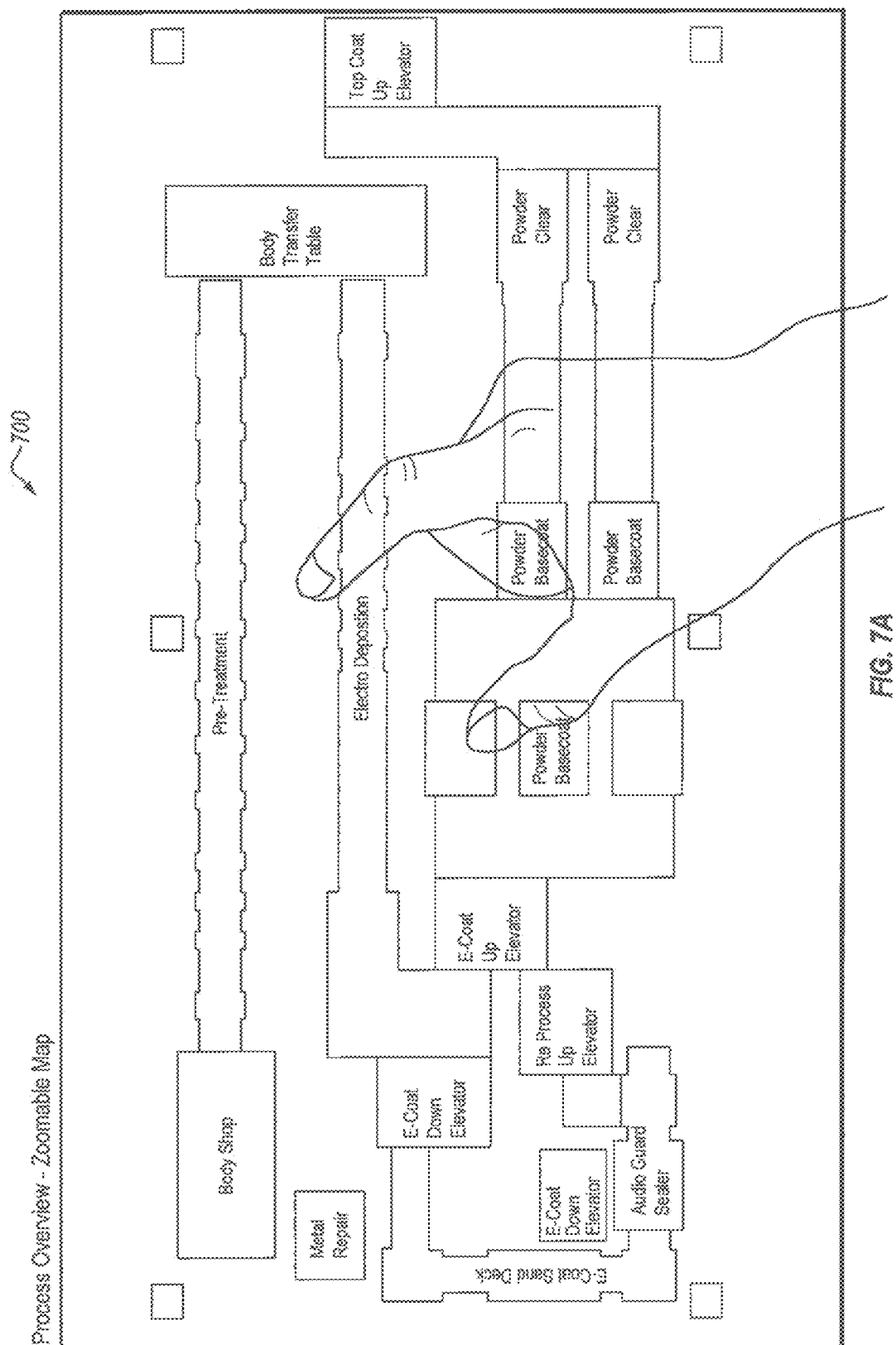
FIG. 7A depicts another paint system user interface in accordance with the present invention.

In addition to providing users with trouble shooting abilities, paint system software 100 can also provide a paint facility manager with an overview of an entire paint facility. For example, FIG. 7A depicts a paint facility schematic interface 700. A paint facility user interface 700 can be customized for any particular paint facility. For example, the user interface 700 can be designed to depict the physical layout of the paint facility, the product progression of the paint facility, or any other layout that is desired by the user.

Figure 7B:
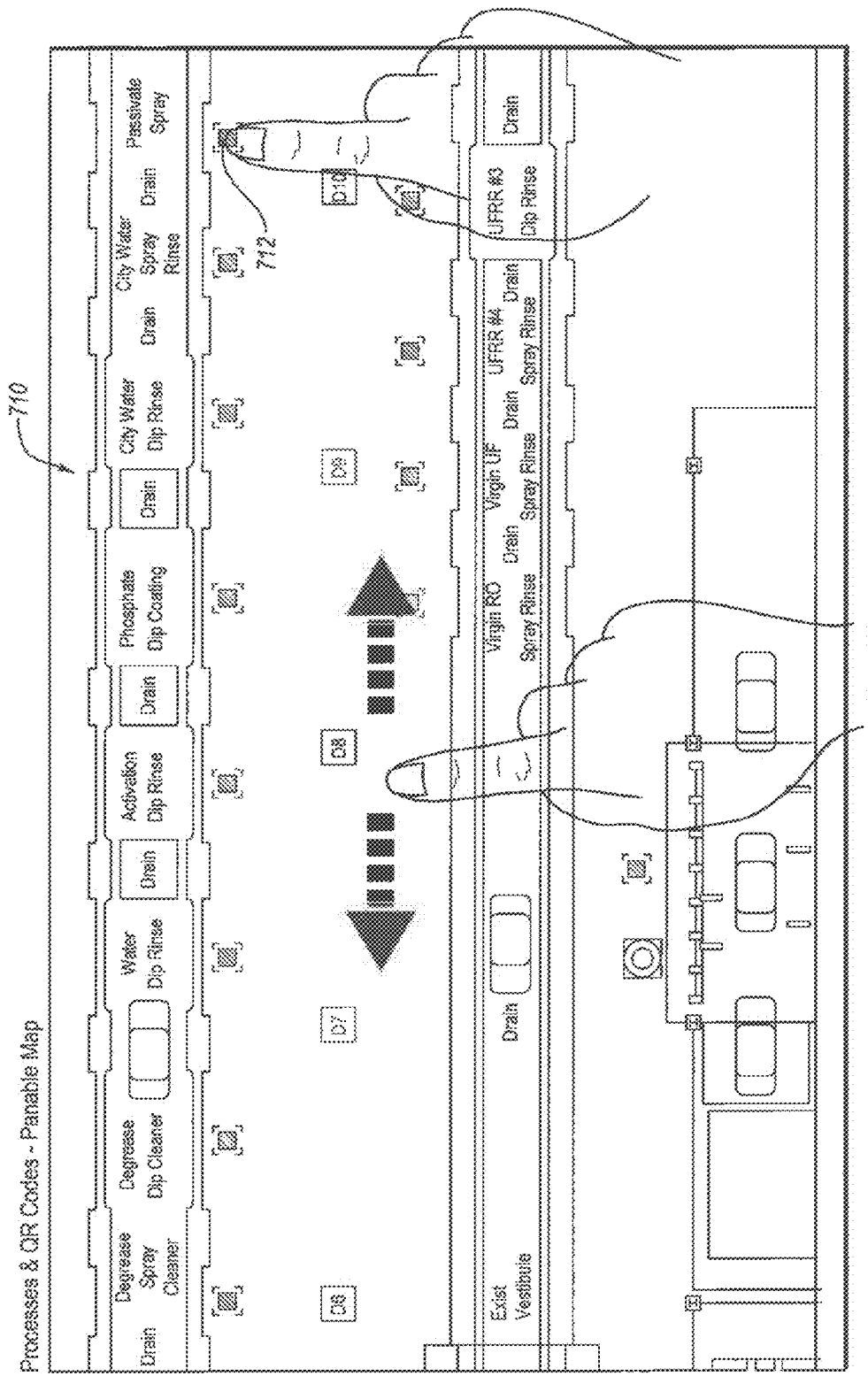
FIG. 7B depicts another paint system user interface in accordance with the present invention.
Figure 7C:
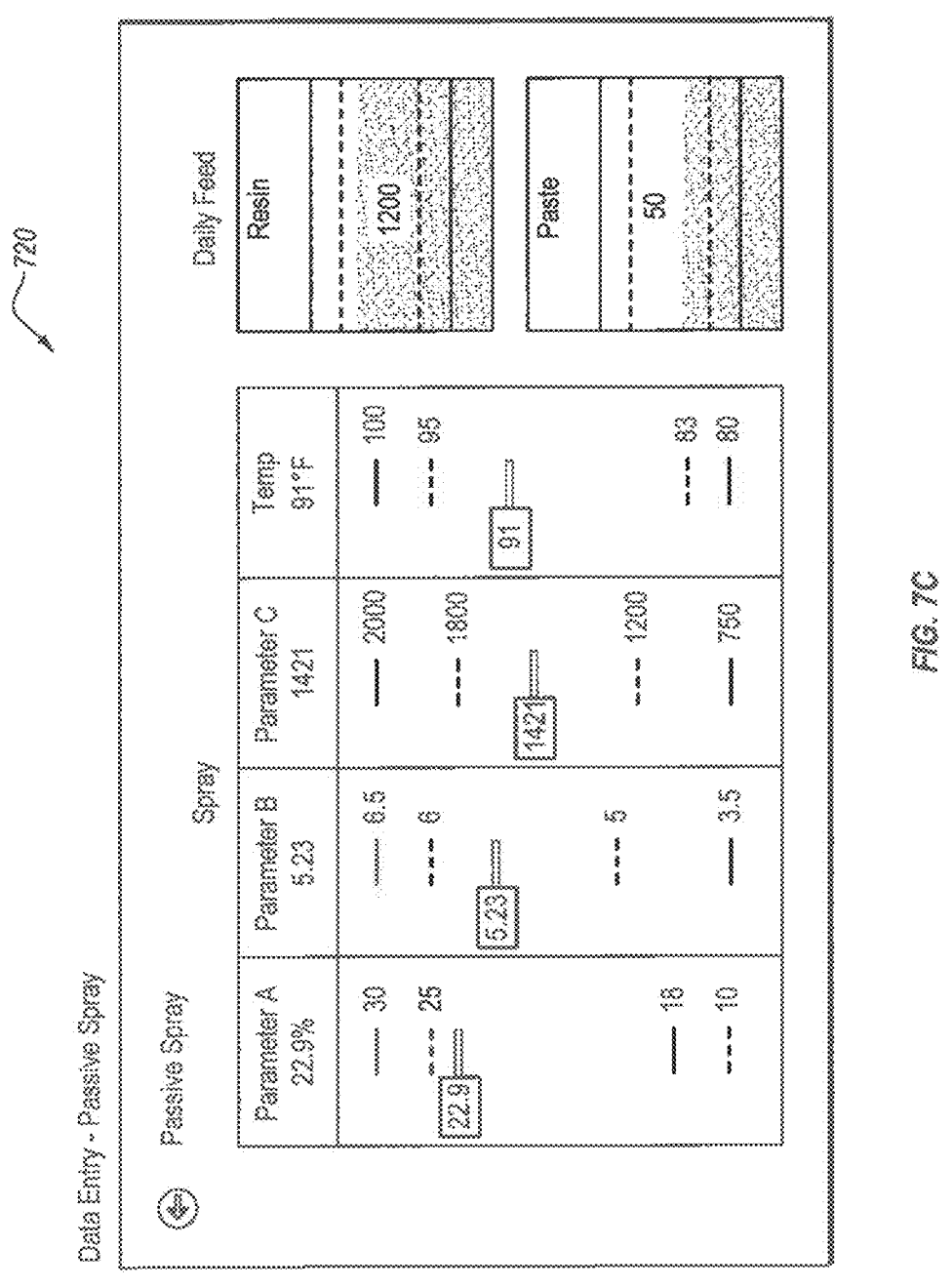

Within the interface 700 of FIG. 7A a user is provided with a physical map of a paint facility. Within the physical map a user can select a particular facility portion to access information relating to that portion. For example, FIG. 7B depicts a zoomed in portion of the map shown in FIG. 7A. The interface of FIG. 7B depicts individual processes 710 that take place within that part of the paint facility. Additionally, a user can be provided with access options 712 to access additional information relating to each individual paint facility process. For example, upon selecting the passive spray process, a passive spray interface 720 as depicted in FIG. 7C may be displayed to a user.

The present invention can provide a variety of task-specific user interfaces. For example, a user can access a user interface that provides the user information about and control of an entire paint facility processing line. Similarly, a user can access another user interface that provides the user with alerts relating to the current paint application process. As such, the present invention provides dynamic and novel methods for controlling and monitoring a paint facility and paint application process.

Accordingly, FIGS. 1-7C and the corresponding text illustrate or otherwise describe one or more methods, systems, and/or instructions stored on a storage medium for monitoring and managing one or more paint facilities. One will appreciate that the present invention can also be described in terms of methods comprising one or more acts for accomplishing a particular result. For example, FIGS. 8 and 9 and the corresponding text illustrate flowcharts of a sequence of acts in a method for monitoring and managing one or more paint facilities. The acts of FIGS. 8 and 9 are described below with reference to the components and modules illustrated in FIGS. 1-7C.

Figure 8:
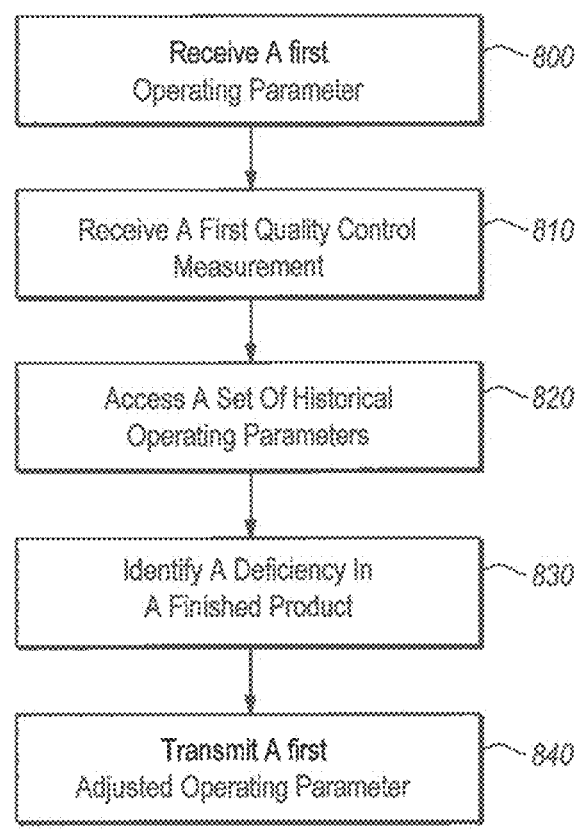
FIG. 8 is a flowchart of an exemplary method implemented in accordance with the present invention.
Figure 9:
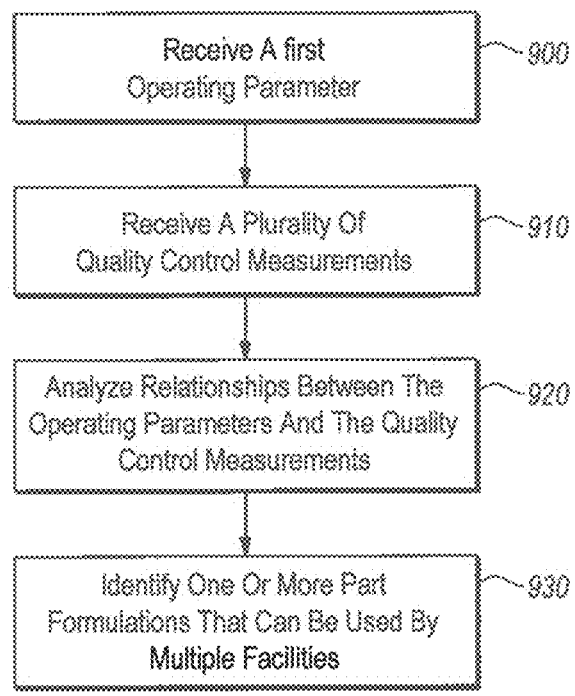
FIG. 9 is a flowchart of another exemplary method implemented in accordance with the present invention.

For example, FIG. 8 illustrates that a flow chart for a method for receiving data and providing calculated adjustments to the paint application process can comprise an act 800 of receiving a first operating parameter. Act 800 can include receiving at the server, from a computing device, a first operating parameter associated with a first paint processing machine at a first painting facility. For example, FIG. 1 and the accompanying description, illustrate that a quality assurance database 112 can comprises various operating parameters, such as thresholds, best practices, paint application machinery specifications, paint formulations, and other related data points. In particular, the quality assurance database 112 can comprise an operating parameter associated with a particular piece of paint application machinery.

Additionally, FIG. 8 depicts that the method can include an act 810 of receiving a first quality control measurement. Act 810 can comprise receiving at the server a first quality control measurement from an analysis of a finished first paint product. For example, FIG. 1 and the accompanying description, illustrates that a camera or spectrophotometer sensor 122 can communicate various quality control measurements to paint system software 100.

FIG. 8 also depicts that the method can include an act 820 of accessing a set of historical operating parameters. Act 820 can comprise accessing from a database a set of historical operating parameters associated with the first painting processing machine. For example, FIG. 1 and the accompanying description, illustrates a quality assurance processing module 110. The quality assurance processing module 110 can receive historical operating data from the quality assurance database 112. The historical operating parameters may comprise machinery operation parameters, previously made adjustments, historic output data, and other similar data.

Further, FIG. 8 depicts that the method can include an act 830 of identifying a deficiency in a finished product. Act 830 can comprise automatically identifying a deficiency in the finished first paint product based upon the first quality control measurement. For example, FIG. 1 and the accompanying description, illustrates that the quality assurance processing module 110 can identify a deficiency in a finished product based upon information received from the sensor module 120. For instance, the quality assurance module may determine that a film thickness is outside of specified thresholds.

Further still, FIG. 8 depicts that the method can include an act 840 of transmitting a proposed adjustment. Act 840 can comprise transmitting to a computing device screen a proposed adjustment to the first operating parameter that will correct the deficiency. The proposed adjustment can account for the historical operating parameters associated with the first paint processing machine. For example, FIG. 1 and the accompanying description illustrate an IO module 140 that communicates proposed adjustments to a computing device 142. For instance, the user interfaces 450, 500 of FIGS. 4 and 5 depict examples of suggested changes.

In addition to the foregoing, FIG. 9 illustrates a flow chart for an additional or alternative method for receiving data and providing calculated adjustments to a paint application process. For example, FIG. 9 shows that the method can comprise an act 900 of receiving one or more operating parameters from a plurality of facilities. Act 900 can comprise receiving at a server from a plurality of painting facilities one or more operating parameters that are unique to each respective painting facility. For example, FIG. 2 and the accompany description illustrate a remote server 144 in communication with various paint facilities 200(a-e) spread out across a geographically diverse area. The remote server 144 can receive operating parameters from each of the unique paint facilities 200(a-e).

Additionally, FIG. 9 shows that the method can include an act 910 of receiving a plurality of quality control measurements. Act 910 can comprise receiving a plurality of quality control measurements from analyses of finished paint products from each respective painting facility. For example, each paint facility 200(a-e) can comprise its own paint system software 100. Each respective paint system software 100 can comprise an IO module 140 that communicates with the remote server 144. Specifically, the IO module 140 can communicate to the remote server 144 information, such as quality control measurements.

FIG. 9 also shows that the method can include an act 920 of analyzing relationships between the operating parameters and the quality control measurements. Act 920 can comprise automatically analyzing, with one or more processors, relationships between historic operating parameters and historic quality control measures at each of the painting facilities. For example, FIG. 2 and the accompanying description, describe the remote server 144 as analyzing the information received the paint facilities 200(a-e) to identify various trends.

Further, FIG. 9 shows that the method can include an act 930 of identifying one or more paint formulations that can be used by multiple facilities. Act 930 can comprise, based upon the analyzed relationships, identifying one or more initial paint formulas that can be utilized by at least two of the plurality of painting facilities and which are capable of creating a particular paint product that meets predetermined parameters. For example, FIG. 2 and the accompanying description describe an example where the remote server 144 determines that the same paint formulation can be used by paint facility 200a and the paint facility 200e to create the same final coatings, albeit with different operating parameters at each facility 200a, 200e.

Accordingly, the present invention can provide significant advantages over conventional systems and methods, and address many long-felt needs. For example, the present invention can automatically identify negative trends within a paint application facility. Additionally, the present invention can perform multivariate analysis to identify potential changes that can be made to avoid negative outcomes. Further, the present invention can identify efficiencies that can be implemented across geographically diverse and operationally unique paint facilities.

Although the subject matter has been described in language specific to structural features and/or methodological acts, it is to be understood that the subject matter defined in the appended claims is not necessarily limited to the described features or acts described above, or the order of the acts described above. Rather, the described features and acts are disclosed as example forms of implementing the claims.

The present invention may comprise or utilize a special-purpose or general-purpose computer system that includes computer hardware, such as, for example, one or more processors and system memory, as discussed in greater detail below. The present invention may also include physical and other computer-readable media for carrying or storing computer-executable instructions and/or data structures. Such computer-readable media can be any available media that can be accessed by a general-purpose or special-purpose computer system. Computer-readable media that store computer-executable instructions and/or data structures are computer storage media. Computer-readable media that carry computer-executable instructions and/or data structures are transmission media. Thus, by way of example, and not limitation, the present invention can comprise at least two distinctly different kinds of computer-readable media: computer storage media and transmission media.

Computer storage media are physical storage media that store computer-executable instructions and/or data structures. Physical storage media include computer hardware, such as RAM, ROM, EEPROM, solid state drives ("SSDs"), flash memory, phase-change memory ("PCM"), optical disk storage, magnetic disk storage or other magnetic storage devices, or any other hardware storage device(s) which can be used to store program code in the form of computer-executable instructions or data structures, which can be accessed and executed by a general-purpose or special-purpose computer system to implement the disclosed functionality of the invention.

Transmission media can include a network and/or data links which can be used to carry program code in the form of computer-executable instructions or data structures, and which can be accessed by a general-purpose or special-purpose computer system. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer system, the computer system may view the connection as transmission media. Combinations of the above should also be included within the scope of computer-readable media.

Further, upon reaching various computer system components, program code in the form of computer-executable instructions or data structures can be transferred automatically from transmission media to computer storage media (or vice versa). For example, computer-executable instructions or data structures received over a network or data link can be buffered in RAM within a network interface module (e.g., a "NIC"), and then eventually transferred to computer system RAM and/or to less volatile computer storage media at a computer system. Thus, it should be understood that computer storage media can be included in computer system components that also (or even primarily) utilize transmission media.

Computer-executable instructions comprise, for example, instructions and data which, when executed at one or more processors, cause a general-purpose computer system, special-purpose computer system, or special-purpose processing device to perform a certain function or group of functions. Computer-executable instructions may be, for example, binaries, intermediate format instructions such as assembly language, or even source code.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, tablets, pagers, routers, switches, and the like. The invention may also be practiced in distributed system environments where local and remote computer systems, which are linked (either by hardwired data links, wireless data links, or by a combination of hardwired and wireless data links) through a network, both perform tasks. As such, in a distributed system environment, a computer system may include a plurality of constituent computer systems. In a distributed system environment, program modules may be located in both local and remote memory storage devices.

Those skilled in the art will also appreciate that the invention may be practiced in a cloud-computing environment. Cloud computing environments may be distributed, although this is not required. When distributed, cloud computing environments may be distributed internationally within an organization and/or have components possessed across multiple organizations. In this description and the following claims, "cloud computing" is defined as a model for enabling on-demand network access to a shared pool of configurable computing resources (e.g., networks, servers, storage, applications, and services). The definition of "cloud computing" is not limited to any of the other numerous advantages that can be obtained from such a model when properly deployed.

A cloud-computing model can be composed of various characteristics, such as on-demand self-service, broad network access, resource pooling, rapid elasticity, measured service, and so forth. A cloud-computing model may also come in the form of various service models such as, for example, Software as a Service ("SaaS"), Platform as a Service ("PaaS"), and Infrastructure as a Service ("IaaS"). The cloud-computing model may also be deployed using different deployment models such as private cloud, community cloud, public cloud, hybrid cloud, and so forth.

A cloud-computing environment may comprise a system that includes one or more hosts that are each capable of running one or more virtual machines. During operation, virtual machines emulate an operational computing system, supporting an operating system and perhaps one or more other applications as well. Each host may include a hypervisor that emulates virtual resources for the virtual machines using physical resources that are abstracted from view of the virtual machines. The hypervisor also provides proper isolation between the virtual machines. Thus, from the perspective of any given virtual machine, the hypervisor provides the illusion that the virtual machine is interfacing with a physical resource, even though the virtual machine only interfaces with the appearance (e.g., a virtual resource) of a physical resource. Examples of physical resources including processing capacity, memory, disk space, network bandwidth, media drives, and so forth.

The present invention may be embodied in other specific forms without departing from its spirit or essential characteristics. The above description should be considered in all respects only as illustrative and not restrictive. The scope of the invention is, therefore, indicated by the appended claims rather than by the foregoing description. All changes which come within the meaning and range of equivalency of the claims are to be embraced within their scope.

The present invention may thus relate in particular, without being limited thereto, to the following clauses 1-15:

Clause 1. A system for monitoring and controlling one or more paint application process(es), the system comprising: a first paint application system by which a first painted product is formed from an object to be painted in a first paint application process, one or more first measuring device(s) for determining at least one attribute of the first painted product; a first paint application process database which comprises historical data of the at least one attribute of the first painted product in relation to a plurality of operating parameters associated with the first paint application process including at least environmental conditions, paint ingredients, and operating parameters of the first paint application system; a quality assurance database which comprises data on an ideal range and/or an acceptable range for the at least one attribute of the first painted product; one computing device being configured to, or more than one communicatively linked computing devices being in their entirety configured to: automatically determine the at least one attribute of the first painted product by means of the one or more first measuring device; detect a deficiency in the first painted product by means of a quality assurance processing module, which is in communication with the one or more first measuring device, has access to the quality assurance database and is configured to detect said deficiency by determining if one or more of the determined at least one attribute of the first painted product falls outside of its ideal range and/or its acceptable range; provide a proposed adjustment to one or more operating parameter(s) associated with the first paint application process for correcting said deficiency in the first painted product by means of a paint application system configuration module, which is in communication with the quality assurance processing module and the first paint application system, has access to the first paint application process database and is configured to perform a first multivariate analysis based on the historical data from the first paint application process database for providing the proposed adjustment, wherein the multivariate analysis accounts for at least current environmental conditions, paint ingredients and operating parameters of the first paint application system of the first paint application process; and transmit the proposed adjustment to one or more operating parameter(s) associated with the first paint application process to a display device configured to display the proposed adjustment and/or automatically adjust one or more operating parameter(s) associated with the first paint application process according to the proposed adjustment by the paint application system configuration module.

Clause 2. The system according to clause 1, wherein the first paint application system comprises at least one paint application device that is associated with a plurality of adjustable parameters, wherein optionally the paint application system configuration module is configured to automatically adjust at least one of the adjustable parameters of the one or more paint application device(s) to align with the proposed adjustment; and/or at least a portion of the historical data of the first paint application process database are related to operating parameters of the first paint application system that are specific to type and make of the at least one paint application device.

Clause 3. The system according to any one of clause 1 or 2, further comprising one or more first sensor(s) for determining one or more of the operating parameter(s) associated with the first paint application process, wherein the sensor module is in communication with the one or more first sensors and is configured to automatically measure one or more of the operating parameters associated with the first paint application process.

Clause 4. The system according to any one of clauses 1 to 3, wherein the paint application system configuration module is configured to repeatedly provide proposed adjustments and automatically adjust one or more operating parameter(s) associated with the first paint application process to align with the respective proposed adjustment for correction of a determined deficiency in the first painted product, the configuration module being configured to update the multivariate analysis on the basis of a feedback loop, which takes into account the measured one or more attribute(s) of a first painted product obtained by application of the adjusted one or more operating parameter(s) according to the respective last preceding proposed adjustment in the first paint application process.

Clause 5. The system according to any one of clauses 1 to 4, further comprising: a second paint application system by which a second painted product is formed from an object to be painted in a second paint application process, the second paint application system being in a geographically different location than the first paint application system; one or more second measuring device(s) for determining at least one attribute of the second painted product and a second paint application process database which comprises historical data of one or more second painted product attribute(s) in relation to a plurality of operating parameters associated with the second paint application process including at least environmental conditions, paint ingredients and operating parameters of the second paint application system, and one or more computing device(s) configured to provide the analogous functions as defined in any one of claims 1 for the first paint application process with respect to the second paint application process; and a server in communication with the first paint application system and the second paint application system and having access to the first paint application process database and optionally to the second application process database, wherein the server is configured to: receive an indication of a target paint coating to be applied in the first paint application process and the second paint application process, the target paint coating being associated with a plurality of attribute requirements within predetermined thresholds, identify on the basis of data comprising the historical data from the first paint application process database and optionally the second paint application process database first operating parameters associated with the first paint application process and second operating parameters associated with the second paint application process for creating the target paint coating by the first paint application process as well as by the second paint application process such that said plurality of attribute requirements are fulfilled within the predetermined thresholds, wherein the identified first operating parameters are different from the identified second operating parameters.

Clause 6. The system according to clause 5, wherein the server is configured to identify a common paint formulation for the target paint coating that both the first paint application system and the second paint application system are capable of using to create the target paint coating such that said plurality of attribute requirements are fulfilled within the predetermined thresholds.

Clause 7. The system according to any one of clause 5 or 6, wherein the server is configured to take into account local meteorological conditions in identifying the first operating parameters and the second operating parameters for creating the target paint coating by the first paint application process as well as by the second paint application process such that said plurality of attribute requirements are fulfilled within the predetermined thresholds.

Clause 8. A computer-implemented method for monitoring and controlling one or more paint application process, the method comprising: receiving by a computing device one or more operating parameter(s) associated with a first paint application process, wherein a first painted product is formed from an object to be painted by means of a first paint application system; measuring at least one attribute of the first painted product; transmitting the measured at least one attribute of the first painted product to the computing device; automatically detecting a deficiency in the first painted product by determining if one or more of the measured at least one attribute of the first painted product falls outside of its ideal range and/or its acceptable range, said ranges being accessible from a quality assurance processing module; accessing from a first paint application process database a set of historical data of the at least one attribute of the first painted product in relation to one or more operating parameter(s) associated with the first paint application process; providing based on said historical data a proposed adjustment to at least one of the one or more operating parameter(s) associated with the first paint application process for correcting said deficiency; and displaying the proposed adjustment on a display device and/or automatically adjusting one or more operating parameter associated with the first paint application process according to the proposed adjustment.

Clause 9. The method according to clause 8, wherein the computing device comprises a server.

Clause 10. The method according to clause 9, further comprising: receiving by the server one or more operating parameter associated with a second paint application process, wherein a second painted product is formed from an object to be painted by means of a second paint application system, the second paint application system being in a geographically different location than the first paint application system; measuring at least one attribute of the second painted product; transmitting the measured at least one attribute of the second painted product to the server; storing the received measured painted product attributes and corresponding operating parameters; automatically analyzing the stored information for relationships between historic measured painted product attributes and historic operating parameters for both the first paint application process and the second paint application process; receiving by the server an indication of a target paint coating to be applied in the first paint application process and the second paint application process, the target paint coating being associated with a plurality of attribute requirements within predetermined thresholds, identifying, based on the analyzed relationships, at least one paint formulation that can be utilized in both the first paint application process and the second paint application process to create the target paint coating such that said plurality of attribute requirements are fulfilled within the predetermined thresholds.

Clause 11. The method according to clause 10, wherein the first paint application system comprises at least one first paint application device, and the second paint application system comprises at least one second paint application device that is of a different type and make than the first paint application device, and the method further comprises: adjusting one or more operating parameter of the first paint application system based upon the type and make of the first paint application device and/or adjusting one or more operating parameter of the second paint application system based upon the type and make of the second paint application device.

Clause 12. The method according to any one of clause 8 to 11, comprising adjusting one or more operating parameter(s) associated with the first paint application process based upon current meteorological conditions at the geographical location of the first paint application system, optionally further comprising adjusting one or more operating parameter(s) associated with the second paint application process, if any, based upon current meteorological conditions at the geographical location of the second paint application system, if any.

Clause 13. A computer-readable medium comprising computer-executable instructions that when executed by a computing device cause the computing device to implement a method according to any one of clause 8 to 12.

Clause 14. A computer-readable medium comprising computer-executable instructions that when executed by a computing device cause the computing device to implement a method, which comprises: receiving by a server from a plurality of paint application processes each one or more operating parameter(s) associated with the respective paint application process, wherein in each paint application process a painted product is formed from an object to be painted by means of a paint application system; measuring at least one attribute of the painted product for each paint application process; transmitting the measured at least one attribute of the painted product to the server; storing the received measured at least one attribute of the painted product and corresponding operating parameters; automatically analyzing the stored information for relationships between historic measured painted product attributes and historic operating parameters for each of the plurality of paint application processes; receiving by the server an indication of a target paint coating to be applied in the paint application processes, the target paint coating being associated with a plurality of attribute requirements within predetermined thresholds, identifying, based on the analyzed relationships, at least one paint formulation that can be utilized in at least two of the plurality of paint application processes to create the target paint coating such that said plurality of attribute requirements are fulfilled within the predetermined thresholds.

Clause 15. A computer-readable medium according to clause 14, wherein the historic operating parameters of each of the plurality of paint application processes are associated with the local meteorological conditions at the geographical location of the respective paint application system and/or are associated with the paint application system utilized in the respective paint application process.

We claim:

1. A computerized system for monitoring a paint application process at a first plant and automatically adjusting paint parameters within a first paint application system based upon sensor data gathered from various first sensor modules receiving data from various points within the first paint application system, the system comprising:
a quality assurance parameter database, the quality assurance parameter database being configured to provide an indication of an ideal range of a final paint product attribute;
an electronic sensor module configured to automatically measure the final paint product attribute on a completed product;
a quality assurance processing module configured to:
receive the measured final paint product attribute from the electronic sensor module over a network, and
determine that the measured final paint product attribute is outside of the ideal range;
a paint application system configuration module configured to:
access a first plant database of one or more operating parameters from one or more paint application machines that performed a step in the process of painting the completed product and one or more paint mixture ingredients that were used in the process of painting the completed product, and
determine, using a first multivariate analysis, at least one of the one or more first operating parameters that if adjusted would place the final paint product parameter for future products within the ideal range, wherein the multivariate analysis accounts for at least (i) current environmental conditions, (ii) machine operation parameters, and (iii) paint ingredients; and a mobile computing device comprising a screen that is configured to display a proposed adjustment to at least one operating parameter, wherein the proposed adjustment is received from the paint application system configuration module;

wherein the paint application system sends a determined solution to an atomizer, the determined solution causing the atomizer to automatically change paint delivery based on the determined one or more first operating parameters.

2. The system as recited in claim 1, wherein:
at least one of the paint application machines comprises the atomizer, the atomizer being associated with a plurality of adjustable operating parameter; and
the determined solution comprises a change in paint chemical formulation to be applied by the atomizer.

3. The system as recited in claim 2, further comprising automatically adjusting at least one of the plurality of adjustable operating parameters associated with the atomizer to align with the proposed adjustment.

4. The system as recited in claim 2, wherein at least a portion of the one or more operating parameters from the machinery database are specific to a type and make of the atomizer.

5. The system as recited in claim 1, wherein:
the paint application system configuration module is further configured to update the multivariate analysis; and
the multivariate analysis is based upon a feedback loop indicating an updated final paint product parameter on a recently completed product that was painted using at least one adjusted parameter of the one or more operating parameters.

6. The system as recited in claim 1, further comprising:
a second paint application system configured to monitor a paint application process at a second plant, wherein the second paint application system is in a geographically different location than the first paint application system; and
a central data processing hub in communication with the first paint application system and the second paint application system, wherein the central processing hub is configured to:
receive an indication of a particular paint coating, wherein the paint coating is associated with various threshold attribute requirements, and
identify various first operating parameters from the first plant and various second operating parameters from the second plant required to respectively create the particular paint coating such that it falls within the various threshold attribute requirements;
wherein the first operating parameters and the second operating parameters are different, and relate to different application of a particular color based on different weather characteristics between the first and second paint application systems.

7. The system as recited in claim 6, wherein the central data processing hub is further configured to:
identify various first operating parameters from the first plant and various second operating parameters from the second plant required to respectively create the particular paint coating, such that it falls within the various threshold attribute requirements;
wherein both the first plant and the second plan utilize a common paint formulation for the particular color.

8. The system as recited in claim 7, wherein at least one of the first operating parameters and the second operating parameters are influenced by local meteorological conditions.

9. The system as recited in claim 6, wherein the central data processing hub is further configured to:
identify a common paint formulation for the particular color that both the first plant and the second plant are capable of using to create the particular paint coating such that it falls within the various threshold attribute requirements;
wherein the first and second paint application systems apply the particular color on a target differently based on different local geographic conditions.

10. The computerized system as recited in claim 1, wherein the electronic sensor module comprises a spectrophotometer, the system further being configured to:
receive spectrophotometer data from the spectrophotometer; and
further adjust the one or more first operating parameters based on the received spectrophotometer data.

11. The computerized system as recited in claim 1, wherein automatically changing paint delivery based on the determined one or more first operating parameters further comprises automatically adjusting atomization energies.

12. The computerized system as recited in claim 1, wherein automatically changing paint delivery based on the determined one or more first operating parameters further comprises automatically adjusting evaporation energies or cure energies.

13. At a server for monitoring a paint application process, a method for receiving data and providing calculated adjustments to the paint application process, the method comprising:
receiving at the server, from a remote portable computing device, a first operating parameter associated with a first paint processing machine at a first painting facility;
receiving at the server a first quality control measurement from an analysis of a finished first paint product;
accessing from a database a set of historical operating parameters associated with the first painting processing machine;
automatically identifying a deficiency in the finished first paint product based upon the first quality control measurement; and
transmitting to a mobile computing device screen a proposed adjustment to the first operating parameter that will correct the deficiency;
wherein the proposed adjustment accounts for the historical operating parameters associated with the first paint processing machine; and
automatically changing operation of the first paint processing machine by the server, such that the first paint processing machine adjusts paint delivery based on the transmitted first operating parameter.

14. The method as recited in claim 11, further comprising:
receiving, at the server, from a second painting facility one or more operating parameters that are unique to the second painting facility;
receiving, at the server, a second quality control measurement from analyses of finished second paint products from the second painting facility;

automatically analyzing relationships between historic operating parameters and historic quality control measures at both the first painting facility and the second painting facility;

based upon the analyzed relationships, identifying at least one initial paint formulation that can be utilized at both the first painting facility and the second painting facility to create a particular paint coating that is within one or more threshold requirements.

15. The method as recited in claim 13, further comprising automatically instituting the proposed adjustment to the first operating parameter.

16. The method as recited in claim 13, further comprising adjusting the first operating parameter based upon current meteorological conditions at the first painting facility.

17. The method as recited in claim 13, further comprising:
adjusting a second operating parameter based upon current meteorological conditions at the second painting facility;
wherein the adjustment to the first operating parameter is different than the adjustment to the second operating parameter due to different meteorological conditions at the first painting facility and the second painting facility.

18. The method as recited in claim 13, wherein:
the first paint processing machine comprises a first atomizer, and
the second paint processing machine comprises a second atomizer that is a different type and make than the first atomizer.

19. The method as recited in claim 18, further comprising adjusting the first operating parameter based upon a type and make of the first atomizer.

20. The method as recited in claim 19, further comprising:
adjusting a second operating parameter based upon the type and make of the second atomizer;
wherein the adjustment to the first operating parameter is different than the adjustment to the second operating parameter due to different type and make of the first atomizer and the second atomizer;
wherein the adjustment to the first or second operating parameter automatically adjusts operation of the first or second atomizer.

21. The method as recited in claim 13, wherein automatically changing operation of the first paint processing machine to adjust paint delivery further comprises adjusting atomization energies.

22. The method as recited in claim 13, wherein automatically changing operation of the first paint processing machine to adjust paint delivery further comprises automatically adjusting evaporation energies or cure energies.

23. A computer system, comprising:
one or more processors;
system memory; and
one or more computer-readable storage media having stored thereon computer-executable instructions that, when executed by the one or more processors, cause the computer system to implement a method for receiving data and providing calculated adjustments to a paint application process, the method comprising:
receiving at a server from a plurality of painting facilities one or more operating parameters that are unique to each respective painting facility;
receiving a plurality of quality control measurements from analyses of finished paint products from each respective painting facility;
automatically analyzing, with the one or more processors, relationships between historic operating parameters and historic quality control measures at each of the painting facilities;
based upon the analyzed relationships, identifying one or more initial paint formulas that can be utilized by at least two of the plurality of painting facilities and which are capable of creating a particular paint product that meets predetermined parameters; and
transmitting one or more parameter adjustments to at least two of the plurality of painting facilities;
wherein the computer system automatically adjusts (i) operation of a first atomizer at a first painting facility based on one set of local parameters, and (ii) operation of a second atomizer at a corresponding second painting facility based on a different set of local parameters.

24. The method as recited in claim 23, wherein historic operating parameters of each of the plurality of painting facilities are associated with different respective local meteorological conditions.

25. The method as recited in claim 23, wherein historic operating parameters of each of the plurality of painting facilities are associated with different respective paint processing machinery.

26. The method as recited in claim 23, wherein receiving a plurality of quality control measurements further comprises receiving spectrophotometer data from a spectrophotometer sensor, the method further comprising:
adjusting the one or more initial paint formulas based on the received spectrophotometer data.

27. The method as recited in claim 23, wherein receiving a plurality of quality control measurements further comprises receiving data in the form of one or more of (i) near field communication or data capture data, (ii) bar or QR reader data, (iii) one or more voice recordings; or (iv) one or more camera readings:
adjusting the one or more initial paint formulas based on the received quality control measurement data.

28. The method as recited in claim 23, wherein receiving a plurality of quality control measurements further comprises receiving data taken from one or more of (i) a thermometer, (ii) pressure sensor, (iii) depth sensor, (iv) chemical detection sensor, or (v) multi-meter:
adjusting the one or more initial paint formulas based on the received quality control measurement data.

* * * * *

UNITED STATES PATENT AND TRADEMARK OFFICE
CERTIFICATE OF CORRECTION

PATENT NO. : 9,921,206 B2
APPLICATION NO. : 14/695459
DATED : March 20, 2018
INVENTOR(S) : Vincent P. Dattilo et al.

Page 1 of 1

It is certified that error appears in the above-identified patent and that said Letters Patent is hereby corrected as shown below:

In the Claims

Claim 14, Column 20, Line 61:
"claim 11" should be --claim 13--

Signed and Sealed this
Sixth Day of November, 2018

Andrei Iancu
*Director of the United States Patent and Trademark Office*